United States Patent
Handa et al.

(10) Patent No.: US 6,214,997 B1
(45) Date of Patent: Apr. 10, 2001

(54) PROCESS FOR THE PREPARATION OF CRYSTALLINE (Z)-2-(2-TERT.-BUTOXYCARBONYLPROP-2-OXYIMINO)-2-(2-TRIPHENYLMETHYLAMINOTHIAZOL-4-YL) ACETIC ACID IN ASSOCIATION WITH N,N-DIMETHYLFORMAMIDE

(75) Inventors: Vijay Kumar Handa; Surinder Mohan Gupta; Nittin Maheshwari; Amit Rohatgi, all of New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/321,384

(22) Filed: May 27, 1999

(30) Foreign Application Priority Data

Jun. 1, 1998 (IN) .............................. 1471/DEL/18

(51) Int. Cl.⁷ .................................. C07D 277/40
(52) U.S. Cl. ............................................. 548/194
(58) Field of Search ............................... 548/194

(56) References Cited

U.S. PATENT DOCUMENTS

| 4,258,041 | 3/1981 | O'Callaghan et al. |
| 4,493,933 | 1/1985 | Brodie . |
| 4,497,956 | * 2/1985 | Looker ................. 548/194 |
| 4,665,167 | 5/1987 | Looker . |

* cited by examiner

*Primary Examiner*—Robert Gerstl
(74) *Attorney, Agent, or Firm*—Jayadeep R. Deshmukh

(57) ABSTRACT

The present invention relates to the preparation of crystalline (Z)-2-(2-tert.-butoxycarbonyl prop-2-oxyimino)-2-(2-triphenylmethylaminothiazol-4-yl) acetic acid of the following formula

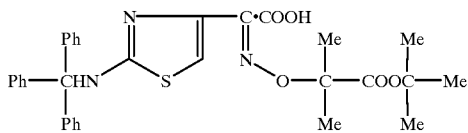

which is useful in the synthesis of β-lactam antibiotics such is ceftazidime.

4 Claims, No Drawings

PROCESS FOR THE PREPARATION OF CRYSTALLINE (Z)-2-(2-TERT.-BUTOXYCARBONYLPROP-2-OXYIMINO)-2-(2-TRIPHENYLMETHYLAMINOTHIAZOL-4-YL) ACETIC ACID IN ASSOCIATION WITH N,N-DIMETHYLFORMAMIDE

FIELD OF THE INVENTION

The present invention relates to the preparation of crystalline (Z)-2-(2-tert.-butoxycarbonyl prop-2-oxyimino)-2-(2-triphenylmethylaminothiazol-4-yl) acetic acid of the following formula:

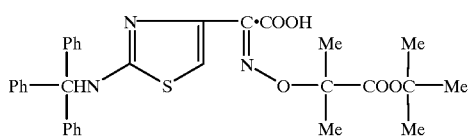

which is useful in the synthesis of β-lactam antibiotics such as ceftazidime.

BACKGROUND OF THE INVENTION

One general method of preparing ceftazidime which is disclosed in U.S. Pat. No. 4,258,041 involves a series of reactions to form the side-chain acid of ceftazidime or a reactive derivative thereof followed by coupling with the 7-β-amino cephalosporin nucleus. Two of the intermediates described in such a series of reactions for the preparation of a protected form of the 7-side chain are (Z)-2-(2-tert.-butoxycarbonylprop-2-oxyimino)-2-(2-triphenylmethylaminothiazol-4-yl) acetic acid and its ethyl ester. However, these intermediates suffer from a number of disadvantages on a manufacturing scale. This material has a variable form which changes on mechanical handling, thus making it difficult to filter satisfactorily.

To overcome the problems faced at a manufacturing scale, an improved form of the intermediate was prepared, such as crystalline (Z)-2-(2-tert.-butoxycarbonylprop-2-oxyimino)-2-(2-triphenylmethylaminothiazol-4-yl)acetic acid associated with 0.1 to 0.6 moles of dioxan per mole of acid. This process is disclosed in U.S. Pat. No. 4,493,933. In U.S. Pat. No. 4,665,167, a crystalline (Z)-2-(2-tert.-butoxycarbonylprop-2-oxyimino)-2-(2-triphenylmethylarinothiazol-4-yl)acetic acid is claimed which contains from 0.8 to 1.8 moles of methanol per mole of acid. The dioxan and methanol-associated acid also suffers from certain disadvantages on a commercial scale. Dioxan and methanol are highly flammable solvents and difficult to handle on a manufacturing scale.

The known methods in the literature for the preparation of (Z)-2-(2-tert.- butoxycarbonylprop-2-oxyimino)-2-(2-triphenylmethylaminothiazol-4-yl)acetic acid (IV) involves the selective hydrolysis of Ethyl (Z)-2-(2-tert.-butoxycarbonylprop-2-oxyimino)-2-(2-triphenylmethylaminothiazol-4-yl)acetate of Formula (VI) (Scheme II).

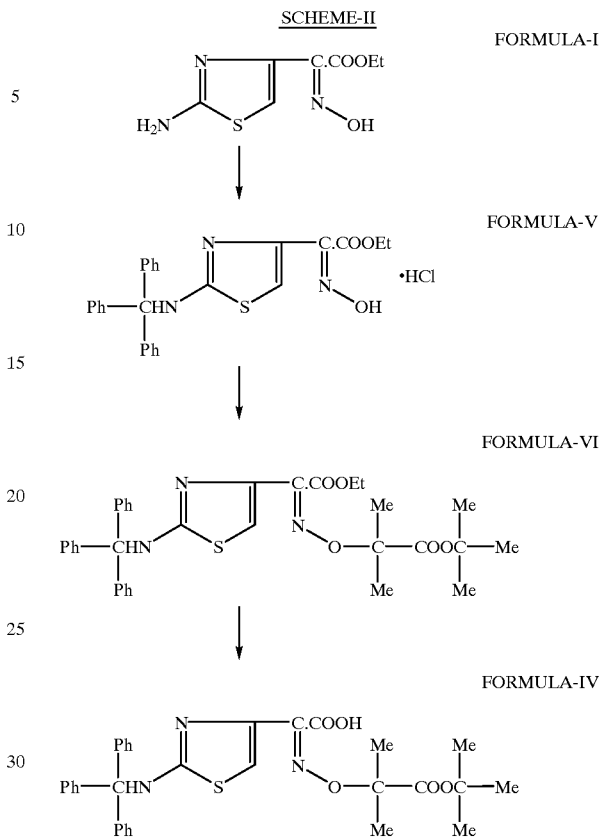

These methods give (Z)-2-(2-carboxylprop-2-oxyimino)-2-(2-triphenylmethylaminothiazol-4-yl) acetic acid as a side product, which is difficult to remove. Removal of this impurity is possible only by repeated crystallizations at the cost of the yield.

SUMMARY OF THE INVENTION

It is an object of the present invention to provide a method for the preparation of the compound of Formula (IV) which eliminates the use of hazardous solvents and is convenient to operate on a manufacturing scale.

It is a further object of the present invention to provide a process which is efficient, cost effective and yields the product in high purity. We have found that new N,N-dimethylformamide-associated acid of Formula (IV) provides a number of advantages on a manufacturing scale. N,N-dimethylformamide is a commercially available solvent and convenient to handle. We have also found that if the process for the preparation of N,N-dimethylformamide-associated acid of Formula (IV) is carried out according to the reaction sequence as shown in Scheme I, side products are formed in minor amounts and the product obtained is very pure.

SCHEME I

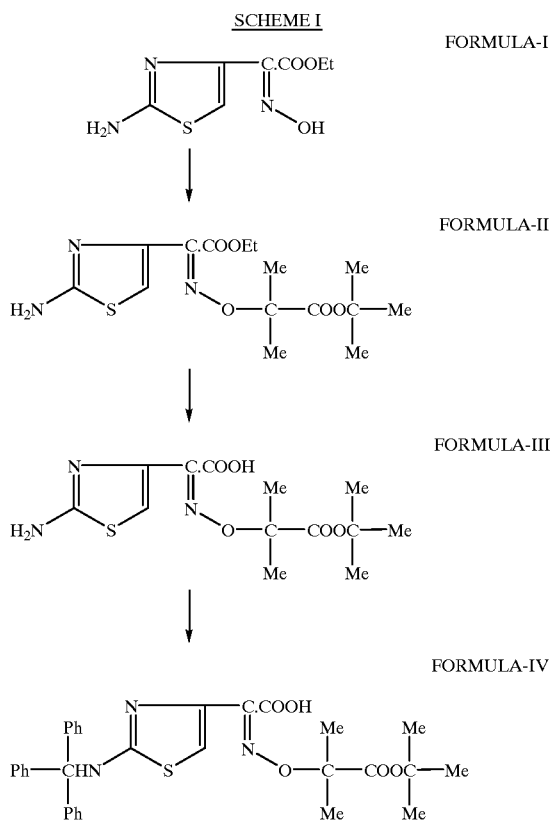

FORMULA-I

FORMULA-II

FORMULA-III

FORMULA-IV

Accordingly the present invention provides a process for the preparation of crystalline (Z)-2-(2-tert.-butoxycarbonylprop-2-oxyimino)-2-(2-triphenylmethylaminothiazol-4-yl) acetic acid of Formula (IV) in association with 0.3 to 0.6 moles of N,N-dimethylformamide per mole of acid which comprises treatment of ethyl (Z)-2-(2-aminothiazol-4-yl)-2-hydroxyiminoacetate of Formula (I) with tert.-butyl-2-bromoisobutyrate to give ethyl (Z)-2-(2-aminothiazole-4-yl)-2-(2-tert.-butoxycarbonylprop-2-oxyimino) acetate of Formula (II), which is converted into acid of Formula (III) followed by tritylation to give a solution of (Z)-2-(2-tert.-butoxycarbonylprop-2-oxyimino)-2-(2-triphenylmethylaminothiazol-4-yl) acetic acid and N,N-dimethylformamide from which the desired compound of Formula (IV) associated with N,N-dimethylformamide is precipitated. Preferably, the precipitation of the compound of Formula (IV) is assisted by addition of water. The compound of Formula (IV) in association with N,N-dimethylformamide prepared in the present invention is in the form of free-flowing material.

The N,N-dimethylformamide-associated acid of Formula (IV) prepared according to the process of the present invention may be coupled with 7β-amino cephalosporin nucleus by methods known in the art to form the desired antibiotic.

Major advantages of the present invention compared to the prior art processes are: (1) the process is safe and convenient to handle at a commercial scale; (2) the process is cost effective; (3) the product obtained has a high degree of purity (>98% HPLC purity); (4) no further purification is required; and (5) yield is high.

The following specific examples illustrate the process of this invention, but they should not be construed as limiting the scope of this invention in any way.

DETAILED DESCRIPTION OF THE INVENTION

EXAMPLE-1

(a) Preparation of Ethyl (Z)-2-(2-aminothiazol-4-yl)-2-(2-tert.-butyoxycarbonylprop-2-oxyimino) acetate (II) (monoblocked ester)

Ethyl (Z)-2-(2-aminothiazol-4-yl)-2-hydroxyiminoacetate (32.25 g) of Formula (I) is dissolved in N,N-dimethylformamide (258 ml) at room temperature. Tert.-butyl 2-bromoisobutyrate (38.47 g) and anhydrous potassium carbonate (47.61 g) are added and the resulting suspension is heated to 40–45° C. for 20–25 hrs. The reaction mass is cooled to 30–32° C. and it is added slowly to water. The resulting slurry is stirred at 25–30° C. for about one and a half hours. The product is filtered, washed with water and dried under reduced pressure. Yield: 50 g (93.37%), water content <1.0% w/w; Chromatographic purity (HPLC) >98%.

(b) Preparation of (Z)-2-(2-Aminothiazol-4-yl)-2-(2-tert.-butoxycarbonylprop-2-oxyimino) acetic acid (III) (monoblocked acid)

To a suspension of monoblocked ester (24.99 g) of Formula (II) in methanol (175 ml), sodium hydroxide solution (1N, 84 ml) is added and the resulting mass is heated at 45–50° C. for 14–16 hrs. The reaction mass is cooled to 20–25° C. and pH is adjusted to 6.8–7.0 with 1N hydrochloric acid. The reaction mass is concentrated to recover methanol under reduced pressure at 40–45° C. The residue is dissolved in water (50 ml); pH is adjusted to 2.0–2.2 with 1N hydrochloric acid and it is stirred for 15–20 minutes at 2–5° C. The resulting product is filtered, washed with water and dried under reduced pressure. Yield: 21 g (91.18% containing 5–6% w/w water).

The product so obtained (18 g) is heated in isopropyl alcohol (81 ml) at 81–82° C. for about 2 hrs. The resulting slurry is cooled to 15° C. and stirred for 1 hr. The product is filtered, washed with isopropyl alcohol (2×9 ml) and dried under reduced pressure at 40–45° C. Purification Yield: 16.04 g (89.11%), water content <0.5% w/w, chromatographic purity (HPLC) >98%.

(c) Preparation of (Z)-2-(2-tert-Butoxycarbonylprop-2-oxyimino)-2-(2-triphenylmethylaminothiazol-4-yl) acetic acid (IV) (diblocked acid)

Monoblocked acid (12.34 g) of Formula (III) is dissolved in N,N-dimethylformamide (58 ml) at room temperature followed by the addition of triphenylchloromethane (15.67 g). Triethylamine (5.68 g) is added slowly in 5–10 minute. The resulting mass is stirred at 40–42° C. for 18–20 hrs. After this period, it is cooled to room temperature and poured in water (250 ml). The product is filtered, washed with water (160 ml) and finally washed with toluene (125 ml). The product is dried under vacuum at 30–35° C. Yield: 18.9 g (88.3%), water content <1% w/w, N,N-dimethylformamide content 4.6%, 0.378 mole per mole of diblocked acid (by $^1$HNMR).

EXAMPLE-2

Preparation of (Z)-2-(2-tert-Butoxycarbonylprop-2-oxyimino)-2-(triphenylmethylaminothiazol-4-yl) acetic acid (IV) (diblocked acid)

To a suspension of (Z)-2-(2-aminothiazol-4-yl)-2-(2-tert-butoxycarbonylprop-2-oxyimino) acetic acid (monoblocked acid) (100 g) prepared as in Example 1 in methylene chloride (1.74 lt) is added triethylamine (33.76 g) slowly at 5–10° to obtain a clear solution. Add triphenylchloromethane (118.5 g) at 5–10° and then mass temperature is raised to 36–38°. The resulting reaction mixture is stirred for 6 hours. It is then cooled to 20–25° and washed with DM water. The organic layer is concentrated and toluene is added to the residue. The resulting slurry is cooled to 20–25° C., the product is filtered, washed with toluene and dried under reduced pressure at 40–45° C. Yield 171 g (98.5% of theory), water <0.2% w/w, assay 96–97% w/w, methylene chloride 2–2.5% w/w and toluene 1–2% w/w.

We claim:

1. A process for the preparation of crystalline (Z)-2-(2-tert.-butoxycarbonylprop-2-oxyimino)-2-(2-triphenylmethylaminothiazol-4-yl) acetic acid of Formula (IV)

FORMULA-IV

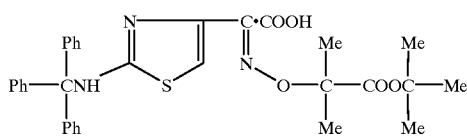

in association with 0.3 to 0.6 moles of N,N-dimethylformamide per mole of acid which comprises treating ethyl (Z)-2-(2-aminothiazol-4-yl)-2-hydroxyiminoacetate of Formula (I)

FORMULA-I

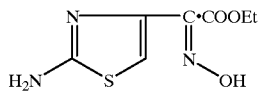

with tert.-butyl 2-bromoisobutyrate to give ethyl (Z)-2-(2-aminothiazol-4-yl)-2-(2-tert.-butoxycarbonyl-prop-2-oxyimino)acetate of Formula (II)

FORMULA-II

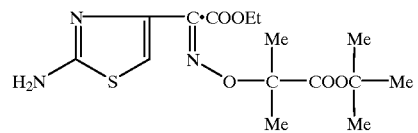

converting said acetate of Formula (II) into acid of Formula (III)

FORMULA-III

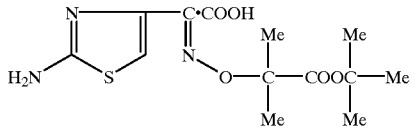

tritylating said acid with triphenylchloromethane to give a solution of (Z)-2-(2-tert-butoxycarbonylprop-2-oxyimino)-2-(2-triphenylmethylaminothiazol-4-yl) acetic acid in N,N-dimethylformamide; and precipitating the desired compound of Formula (IV) associated with N,N-dimethylformamide.

2. A process according to claim 1 wherein precipitation is done by addition of water.

3. The process according to claim 1 wherein the compound of Formula (IV) in association with N,N-dimethylformamide is in the form of a free-flowing material.

4. The process according to claim 2 wherein the compound of Formula (IV) in association with N,N-dimethylformamide is in the form of a free-flowing material.

* * * * *